US007106868B2

(12) United States Patent
Daly

(10) Patent No.: US 7,106,868 B2
(45) Date of Patent: Sep. 12, 2006

(54) ACTIVE NOISE CONTROL FOR VEHICLE DOOR NOISE

(75) Inventor: Paul Desmond Daly, Troy, MI (US)

(73) Assignee: Siemens VDO Automotive Inc., Chatham (CA)

( * ) Notice: Subject to any disclaimer, the term of this patent is extended or adjusted under 35 U.S.C. 154(b) by 740 days.

(21) Appl. No.: 10/405,313

(22) Filed: Apr. 2, 2003

(65) Prior Publication Data

US 2003/0215099 A1 Nov. 20, 2003

Related U.S. Application Data

(60) Provisional application No. 60/380,702, filed on May 15, 2002.

(51) Int. Cl.
*H04R 3/02* (2006.01)
*H04R 27/00* (2006.01)
*A61F 11/06* (2006.01)
*G06F 17/00* (2006.01)

(52) U.S. Cl. ...................... 381/73.1; 381/86; 381/71.4; 381/71.1; 700/94

(58) Field of Classification Search ............... 381/71.1, 381/71.4, 86, 73.1; 181/206, 224; 700/94
See application file for complete search history.

(56) References Cited

FOREIGN PATENT DOCUMENTS

| | | | | |
|---|---|---|---|---|
| JP | 03243437 | A | * | 10/1991 |
| JP | 11149290 | A | * | 6/1999 |
| JP | 2002 023766 | A | | 1/2002 |
| JP | 2002023766 | A | * | 1/2002 |
| WO | WO 01 41123 | A | | 6/2001 |
| WO | WO 200141123 | A1 | * | 6/2001 |
| WO | WO 01 65540 | A | | 9/2001 |
| WO | WO 200165540 | A1 | * | 9/2001 |

OTHER PUBLICATIONS

European Search Report, dated Nov. 20, 2003.

* cited by examiner

*Primary Examiner*—Vivian Chin
*Assistant Examiner*—Devona E. Faulk

(57) ABSTRACT

An active noise control system (100) and method modifies a noise made when a vehicle closure, such as a door, hood, or trunk, closes by detecting the closure's velocity and selecting a delay time and control noise amplitude appropriate for the velocity. By modifying the noise of a vehicle door closing, the system (100) can reduce the frequency and reverberation of the noise generated by the door, improving user perception of the vehicle itself.

16 Claims, 3 Drawing Sheets

ACTIVE NOISE CONTROL FOR VEHICLE DOOR NOISE

REFERENCE TO RELATED APPLICATIONS

This application claims the benefit of U.S. Provisional Appln. No. 60/380,702, filed May 15, 2002.

TECHNICAL FIELD

The present invention is directed to vehicle noise controls, and more particularly to a system that controls the noise created by a vehicle door closing.

BACKGROUND OF THE INVENTION

Vehicle purchasers and owners are often aware of the noise the vehicle door makes when it closes. Many people equate the quality and tone of this sound with the quality of the vehicle, and at least one vehicle manufacturer has even used this sound in its advertising.

More expensive vehicles have vehicle doors made from thicker, heavier metal. As a result, the sound made by these doors when closed tend to have low frequency content with no reverberations. Doors on less expensive vehicles, by contrast, create a noise having higher frequency content and multiple reverberations when closed. The lower frequency noise can be described as a "thunk," while the higher frequency noise can be described as "tinny." The impressions formed by these various noises is intuitive and is often made without any conscious effort by the listener.

Because the sound of the vehicle door closing is so important in creating a favorable user impression of the vehicle, there is a desire for a system that can control and modify the noise of the vehicle door when it closes.

SUMMARY OF THE INVENTION

The present invention is directed to an active noise control system that controls and modifies the noise generated by a closing vehicle door. The system includes a switch, such as a two-stage switch, that indicates the velocity at which the vehicle door is closing. The door velocity is linked to a control noise amplitude so that the system can output a control noise through a speaker near the closing vehicle door.

The frequency spectrum of the control noise itself is selected based on the desired characteristics of the door closing noise. For example, the frequency spectrum of the control noise may be selected to cancel out higher frequency noise and/or reverberations generated when the vehicle door closes. The resulting mixed noise will then have a more pleasing lower frequency spectrum with no reverberation.

In one embodiment, the mixed noise is compared with a template reflecting the desired mixed noise. The control noise is then adjusted based on any deviations between the mixed noise and the template, allowing feedback and correction.

DETAILED DESCRIPTION OF THE EMBODIMENTS

As is known in the art, active noise control systems generally use a speaker to output a generated noise that attenuates one or more undesired noises. The wavelengths in the generated noise are designed to be out-of-phase with the undesired noise, thereby cancelling out the undesired noise's wavelengths when the two noises are mixed together. The generated noise can be created by any known signal generator.

Figure 1:
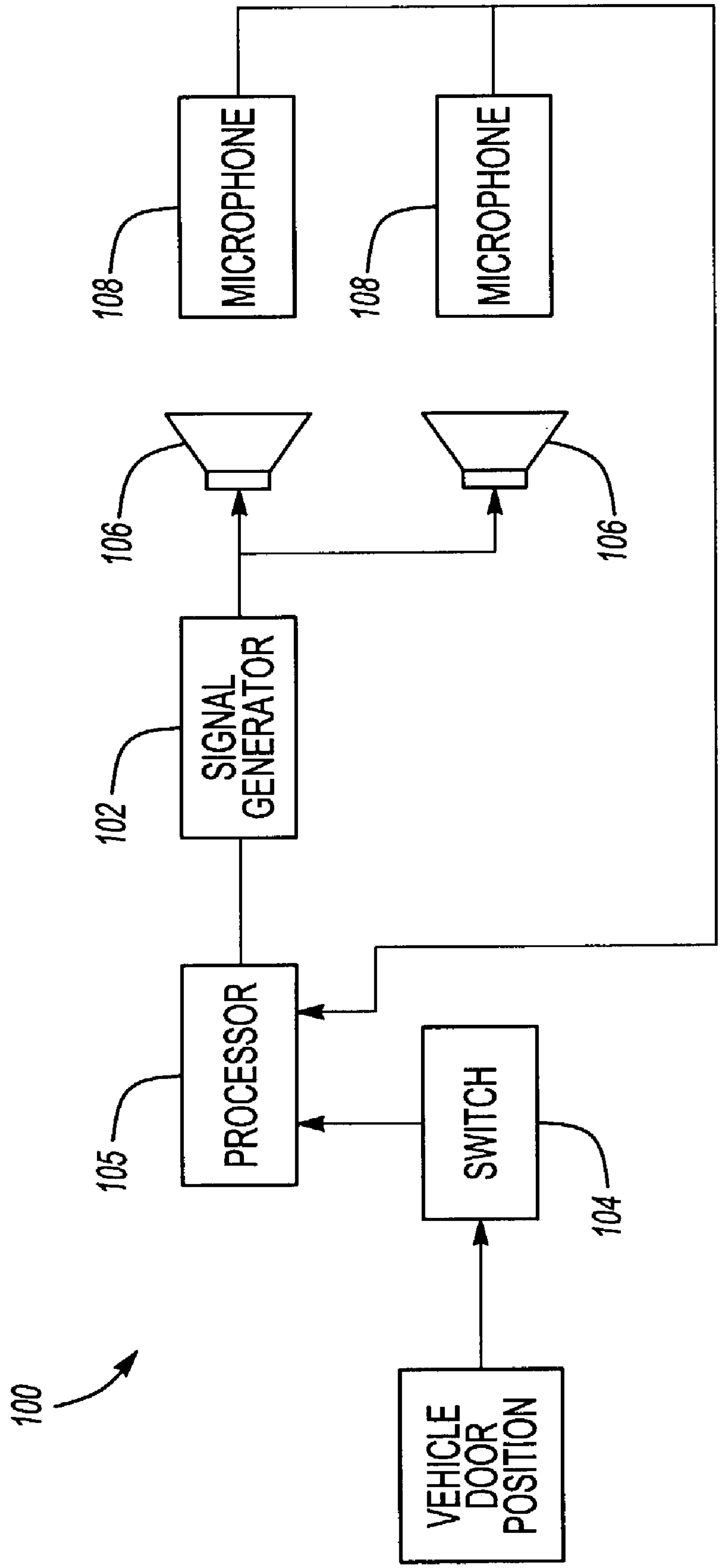
FIG. 1 is a block diagram illustrating components of an active noise control system according to one embodiment of the invention.

The inventive system uses the active noise control concept to control and modify the noises generated by a vehicle door closing. For purposes of this disclosure, the term "vehicle door" includes any vehicle closure, such as a passenger door, lift gate, hood, trunk, etc. FIG. 1 is a block diagram illustrating an active noise control system 100 according to one embodiment of the invention. The system 100 can be part of an overall vehicle sound quality system or can be incorporated into an existing sound system, such as an air induction active noise control (ANC) system and/or an in-car entertainment (ICE) system. Note that if the system 100 is designed to modify noise from various vehicle closures (e.g., door, trunk, lift gate, hood, etc.), the system 100 can incorporate devices from both the air induction ANC system and the ICE system to modify the noise of the vehicle closure.

One embodiment of the system 100 includes a signal generator 102, a switch 104, a processor 105 and one or more speakers 106 that output the noise generated by the signal generator 102. The signal generator 102 may be part of the air induction ANC system or may be a dedicated unit for the inventive system 100. Further, the speakers 106 may themselves be part of the air induction ANC system or the ICE system or may be dedicated units for the inventive system 100. The location of the speakers 106 in the vehicle, as well as the noise output by a given speaker, depends on the specific vehicle closure that is being closed. For example, the system 100 may output a control noise through a speaker in the air induction ANC system for the hood, but may output a control noise through rear speakers in the ICE system for the trunk. The spectral content of the control noise is selected so that the mixture of the actual door closing noise and the control noise has a desired characteristic (e.g., relatively low frequency, no reverberation, etc.).

One or more optional microphones 108 may be included in the system 100 as well. The microphones 108 should be located in an area where they will pick up the mixture of the door closing noise and the control noise.

Figure 2:
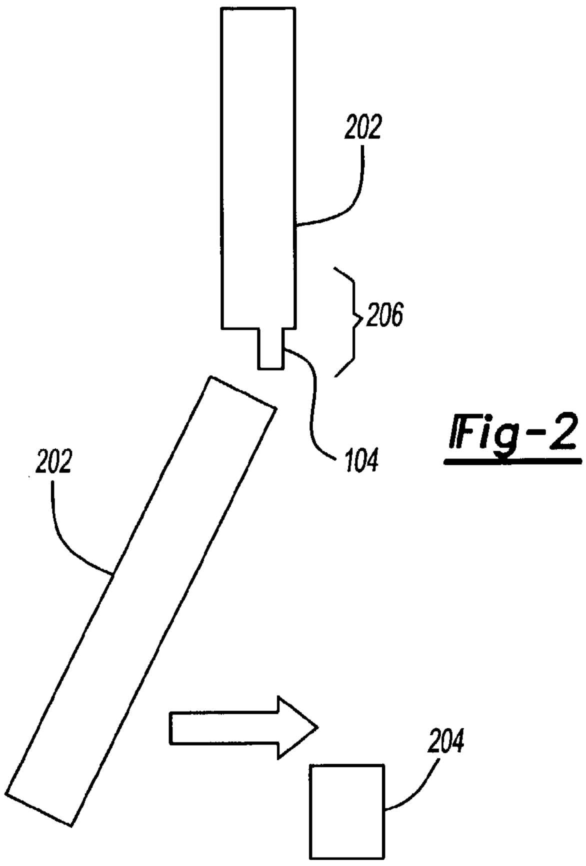
FIG. 2 is a representative diagram illustrating a switch location for one embodiment of the invention.

Note that the noise modification can be conducted via an open loop system or by a closed loop system. FIG. 2 illustrates one possible configuration for triggering active noise control using an open loop system. FIG. 2 shows a vehicle door 200, which swings between an A pillar 202 and a B pillar 204 on a hinge 206. The switch 104 in this example is located on the A pillar 202 and is activated when the door 200 closes, contacting the A pillar 202. In one embodiment, the switch 104 may also control operation of other vehicle components that depend on the vehicle door's position, such as a courtesy light.

Figure 3:
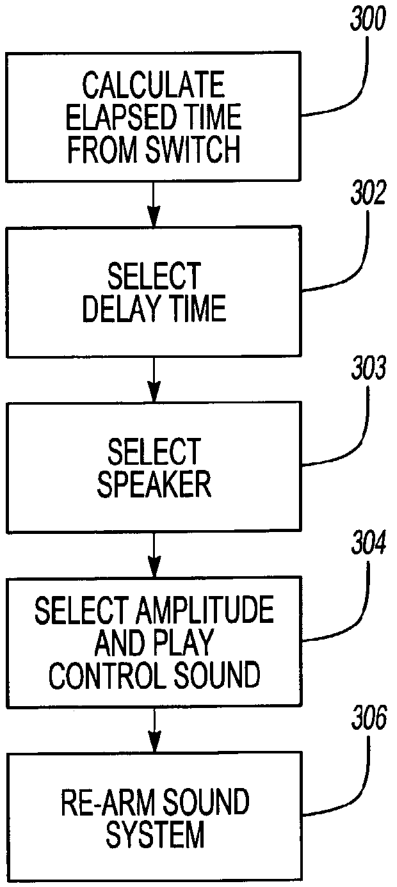
FIG. 3 is a flow diagram illustrating a noise control process according to one embodiment of the invention.

Referring to FIGS. 2 and 3, the system 100 may use a known two-stage switch as the switch 104. A known two-stage switch can be, for example, a piston-like pin that closes a first switch when it is in a first position (e.g., when the pin is pushed halfway between a fully extended and fully depressed position) and closes a second switch when it is in a second position (e.g., the fully depressed position). The first and second switches correspond to first and second positions of the door 202, such as a halfway closed position and a closed position. Alternatively, two separate switches may be used in place of the two-stage switch.

The processor 105 monitors the elapsed time between the closing of the first switch and the closing of the second switch in the two-stage switch 104. This elapsed time corresponds to a door velocity (block 300). If the door is moving quickly, the elapsed time between the two switch closings will be shorter than if the door is moving slowly. The processor 105 then determines an appropriate delay time based on the door velocity as indicated by the elapsed time (block 302); if, for example, the door velocity is high, then the calculated delay time would be smaller than if the door velocity was lower. This delay time coordinates the control noise with the door movement so that the control noise is output at the same time the door fully closes and generates its own noise, which mixes with the control noise.

The processor 105 then selects a speaker 106 for outputting the control noise based on which switch 104 is being closed (block 303). In one embodiment, the processor 105 selects the speaker 106 closest to the vehicle door 200 being closed and ensure that the noise generated by the vehicle door closing is effectively modified. Because each door 200 in the vehicle has its own corresponding switch 104, the processor 105 will be able to tell which door 200 is being closed without requiring any additional sensors in the system.

The processor 105 also selects an appropriate amplitude for the control noise appropriate for the door velocity (block 304). For example, if the two-stage switch 104 indicates that the door 202 is moving quickly, the processor 105 will select a high amplitude to generate a loud, door slamming noise. If the door 202 is moving more slowly, the selected amplitude will be lower. Note that the processor 105 may also check whether the door velocity falls below a selected threshold, indicating that the door is being closed very slowly and will not generate a loud noise; if this occurs, the processor 105 may decide not to output a control noise at all at block 304.

The system 100 then re-arms the sound system so that it is ready to generate another control noise the next time the door 200 is closed (block 306). Note that this re-arming may occur even if no control noise is output at block 304.

Figure 4:
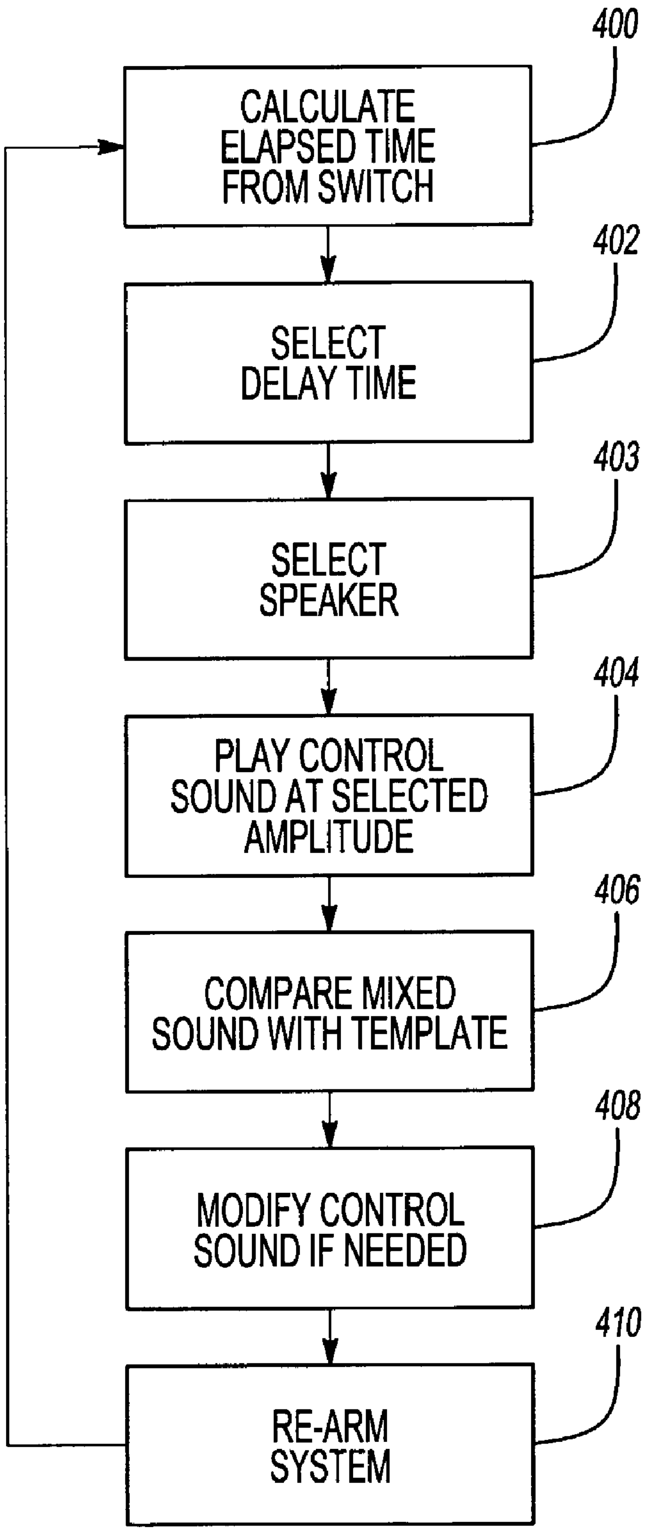
FIG. 4 is a flow diagram illustrating a noise control process according to another embodiment of the invention.

FIG. 4 illustrates another embodiment of the inventive noise control system. In this embodiment, the system is a closed loop, adaptive system that can correct the control noise based on feedback. This embodiment allows the control noise to vary rather than remain fixed, as is the case in an open loop system, thereby improving noise control. The steps of calculating the door velocity from the switch 104 (block 400), selecting a delay time for the control noise output (block 402), selecting a speaker (block 403), and playing the control noise at a selected amplitude (block 404) are the same as in the embodiment of FIG. 3. In this embodiment, however, the microphone 108 captures the mixture of the door noise and the control noise and sends a signal corresponding to this mixed noise back to the processor 105. The processor 105 then compares the signal from the microphone 108 with a template corresponding to the desired mixed noise (block 406). Based on this comparison, the processor 105 instructs the signal generator 102 to modify the control noise if the mixed noise and the template do not match (block 408). The system then re-arms (block 410) and repeats the noise control process using the modified control noise. This feedback allows the system to correct for any deviations between the actual mixed noise and the desired mixed noise.

As a result, the inventive active noise control system modifies the noise of a closing vehicle door to make it more pleasant. The inventive system is not limited to vehicle passenger doors and can be incorporated into any vehicle closure, such as a trunk, hood, and/or lift gate.

It should be understood that various alternatives to the embodiments of the invention described herein may be employed in practicing the invention. It is intended that the following claims define the scope of the invention and that the method and apparatus within the scope of these claims and their equivalents be covered thereby.

What is claimed is:

1. A method of controlling a door noise generated by a closing vehicle door, comprising:

detecting a value corresponding to a door closing velocity;

selecting a control noise output delay time based on the detecting step; and outputting a control noise, wherein the control noise mixes with the door noise to generate a desired mixed noise.

2. The method of claim 1, wherein the detecting step comprises detecting an elapsed time between a first switch position and a second switch position.

3. The method of claim 2, wherein the first switch position corresponds to closing of a first switch and the second switch position corresponds to a closing of a second switch.

4. The method of claim 1, wherein the detecting step comprises detecting an elapsed time between a first switch closing and a second switch closing.

5. The method of claim 1, further comprising selecting a control noise amplitude based on the detecting step.

6. The method of claim 5, wherein the control noise amplitude is zero if the value corresponding to the door closing velocity is below a selected threshold.

7. The method of claim 1, further comprising selecting a speaker in proximity to the closing vehicle door for outputting the control noise.

8. The method of claim 1, further comprising:

comparing the mixed noise with a template; and a modifying characteristic of the control noise based on the comparing step.

9. A method of controlling a door noise generated by a closing vehicle door, wherein the vehicle door is one of a plurality of vehicle doors in a vehicle, comprising:

detecting an elapsed time between a first switch position and a second switch position of a switch activated by the closing vehicle door, wherein the elapsed time corresponds to a door closing velocity;

selecting a control noise output delay time and a control noise amplitude based on the elapsed time;

selecting a speaker corresponding to the closing vehicle door based on activation of the switch; and outputting the control noise through the speaker selected in the selecting step, wherein the control noise mixes with the door noise to generate a desired mixed noise.

10. The method of claim 9, wherein the control noise amplitude is zero if the elapsed time is below a selected threshold.

11. The method of claim 9, further comprising:

comparing the mixed noise with a template; and a modifying characteristic of the control noise based on the comparing step.

12. An active noise control system for controlling a door noise generated by a closing vehicle door in a vehicle, the vehicle having a plurality of speakers, a plurality of vehicle doors and a switch associated with each of the vehicle doors, comprising:

a processor that detects an elapsed time between a first position and a second position of the switch associated with the closing vehicle door and calculates a control noise output delay time and a control noise amplitude based on the elapsed time, wherein the elapsed time corresponds to a door closing velocity; and a signal generator that outputs a control noise output signal to at least one of said plurality of speakers, wherein said at least one speaker outputs a control noise that mixes with the door noise to generate a desired mixed noise.

13. The active noise control system of claim 12, wherein the processor sets the control noise amplitude equal to zero if the elapsed time is below a selected threshold.

14. The active noise control system of claim 12, wherein the switch is a two-stage switch.

15. The active noise control system of claim 12, further comprising at least one microphone that detects the mixed noise, wherein the processor compares the mixed noise with a template and modifies the control noise output signal in the signal generator based on the comparison.

16. The active noise control system of claim 12, wherein the processor selects a speaker closest to the vehicle door to output the control noise.

* * * * *